US007128818B2

(12) United States Patent
Khesin et al.

(10) Patent No.: US 7,128,818 B2
(45) Date of Patent: Oct. 31, 2006

(54) METHOD AND APPARATUS FOR MONITORING GASES IN A COMBUSTION SYSTEM

(75) Inventors: Mark Khesin, Hudson, OH (US); Carl Palmer, Hudson, OH (US); Don Schneider, Lakewood, OH (US); Doug Byrd, Copley, OH (US); Lars Andersson, Cleveland, OH (US)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 10/040,917

(22) Filed: Jan. 9, 2002

(65) Prior Publication Data

US 2003/0127325 A1 Jul. 10, 2003

(51) Int. Cl.
*G01N 27/409* (2006.01)
(52) U.S. Cl. ...................... 204/424; 204/427
(58) Field of Classification Search ............... 204/424, 204/427, 409; 205/784.5; 73/23.31, 23.32
See application file for complete search history.

(56) References Cited

U.S. PATENT DOCUMENTS

| 3,936,648 | A |   | 2/1976  | Cormault et al. |
|-----------|---|---|---------|-----------------|
| 4,039,844 | A |   | 8/1977  | MacDonald       |
| 4,101,403 | A |   | 7/1978  | Kita et al.     |
| 4,177,112 | A |   | 12/1979 | Suzuki et al.   |
| 4,253,404 | A |   | 3/1981  | Leonard         |
| 4,260,363 | A |   | 4/1981  | Cratin, Jr.     |
| 4,296,727 | A |   | 10/1981 | Bryan           |
| 4,370,557 | A |   | 1/1983  | Axmark          |
| 4,419,190 | A | * | 12/1983 | Dietz et al. ................. 205/785 |
| 4,430,192 | A | * | 2/1984  | Maeda ........................ 204/410 |
| 4,562,529 | A |   | 12/1985 | Drummond        |
| 4,639,717 | A |   | 1/1987  | De Meirsman     |
| 4,709,155 | A |   | 11/1987 | Yamaguchi       |
| 4,828,673 | A | * | 5/1989  | Maeda ........................ 204/427 |
| 4,866,420 | A |   | 9/1989  | Meyer, Jr.      |
| 4,885,573 | A |   | 12/1989 | Fry             |
| 4,901,247 | A |   | 2/1990  | Wakimoto        |
| 4,923,117 | A |   | 5/1990  | Adams           |

(Continued)

FOREIGN PATENT DOCUMENTS

DE          4239292 A      5/1994

(Continued)

OTHER PUBLICATIONS

Kimura et al, Principles and Development of a Thick-Film Zirconium Oxide Oxygen Sensor, pp. 101-120 from ACS Symposium Series 309, 1986.*

(Continued)

*Primary Examiner*—Kaj K. Olsen
(74) *Attorney, Agent, or Firm*—Hunton & Williams

(57) ABSTRACT

A method and apparatus for monitoring and measuring gas concentrations in combustor applications is provided, wherein the apparatus is a gas sensor having a plurality of electrodes cooperating with a single electrolyte cell for detecting the presence and concentration of gaseous components of a flue gas. A voltage is generated based on the flow of ions caused by differing gas concentrations as detected by electrodes across the electrolyte. The change in voltage is correlated and is used to determine the concentration of detected gases, such as combustible gases, nitric oxides, carbon monoxide, etc., contained in the flue gas. The combustor operation may then be optimized to enhance efficiency and minimize undesired gas concentrations in the flue gas in a desired fashion. A calibration gas may be introduced to calibrate the apparatus and a reference gas may be provided to an electrode as a basis for correlating the concentrations of the gases.

33 Claims, 6 Drawing Sheets

U.S. PATENT DOCUMENTS

| | | | |
|---|---|---|---|
| 4,944,861 A * | 7/1990 | Reber | 204/428 |
| 5,073,769 A | 12/1991 | Kompelien | |
| 5,076,780 A | 12/1991 | Erdman | |
| 5,077,550 A | 12/1991 | Cormier | |
| 5,107,128 A | 4/1992 | Davall | |
| 5,191,220 A | 3/1993 | Innes | |
| 5,249,954 A | 10/1993 | Allen | |
| 5,257,496 A | 11/1993 | Brown | |
| 5,280,756 A | 1/1994 | Labbe | |
| 5,296,112 A | 3/1994 | Seger et al. | |
| 5,332,386 A | 7/1994 | Hosome | |
| 5,496,450 A | 3/1996 | Blumenthal | |
| 5,501,159 A | 3/1996 | Stevers | |
| 5,599,179 A | 2/1997 | Lindner | |
| 5,705,129 A * | 1/1998 | Takahashi et al. | 422/90 |
| 5,756,059 A | 5/1998 | Zamansky et al. | |
| 5,796,342 A | 8/1998 | Panov | |
| 5,798,946 A | 8/1998 | Khesin | |
| 5,827,415 A | 10/1998 | Gur et al. | |
| 6,067,843 A | 5/2000 | Hafele et al. | |
| 6,103,098 A | 8/2000 | Omara | |
| 6,171,470 B1 | 1/2001 | Patrick | |
| 6,254,749 B1 * | 7/2001 | Yokota et al. | 204/424 |
| 6,277,268 B1 | 8/2001 | Khesin et al. | |
| 6,341,519 B1 | 1/2002 | Khesin | |

FOREIGN PATENT DOCUMENTS

| | | |
|---|---|---|
| EP | 0089630 A | 9/1983 |
| EP | 0 120 423 A1 * | 10/1984 |
| EP | 0 476 601 | 3/1992 |
| EP | 0 581 451 | 2/1994 |
| GB | 2029578 A | 3/1980 |
| WO | WO 97/24560 | 7/1997 |
| WO | 9742495 A | 11/1997 |

OTHER PUBLICATIONS

Khesin, M. J., Ivantotov, A. A., "Fluctuations of Flue Gas Oxygen as Indicator of Combustibles," Teploenetgetika, 1978, 25 (5) 60-63.

Brochure for Miracle Sensor, MPV-2 Combustion Diagnostic System/CO Monitor, Nov. 1997.

M.J Khesin, et al., "Smart Flame Scanners—Myth or Reality?", American Power Conference, Chicago, Apr. 1995.

M.J. Khesin. "Combustion Diagnostics based on Frequency Spectra Analysis", American Flame Research Committee. Montery, CA, Oct. 1995.

Forney Corporation, "OptiFlame Burner Diagnostic System", 1996 Month N.A.

M.J. Khesin, et al., "Demonstration of New Frequency-Based Flame Monitoring System", American Power Conference, Chicago, Apr. 1996.

M.J. Khesin, et al., "Application of a Flame Spectra Analyzer for burner Balancing", Sixth International Joint ISA POWID/EPRI Controls and Instrumentation Conference, Baltimore Jun. 1996.

M.J. Khesin, et al., "Demonstration of New Flame Monitoring System at a Pilot-Scale Gas-Fired Combustion Test Facility", American Flame Research Committee, International Symposium, Baltimore, Md, Sep. 1996.

MK Engineering, Inc., "System may boost combustion efficiency", Industry Watch, Sep. 1996.

M.J. Khesin, et al., "Demonstration Tests of New Burner Diagnostic System on a 650 MW Coal-Fired Utility Boiler", presented at the American Power Conference, Chicago, Apr. 1997.

M.J. Khesin, et al., "Application of a New Burner Diagnostic System for Coal-Fired Utility Boilers", presented to the Joint ISA/EPRI Symposium, Jun.1997, Knoxville, TN.

MK Engineering, Inc., "Combustion Diagnostic System", illustrated brochure distributed Jan. 1998.

MK Engineering, Inc., "Application of MPV-1 Combustion Diagnostic System—A Case Study, Application on a 650 MW Coal-Fired Unit" Jan. 1998.

MK Engineering, Inc. "MPV-1 Combustion Diagnostic System for Tangential Boilers", Jan. 1998.

MK Engineering, Inc., "MPV-1 Combustion Diagnostic System", distributed Feb. 1998.

"Algorithms convert chaos into efficiency", text as printed in Personal Engineering and Instrumentation, Apr. 1998.

M.J. Khesin et al., "Combustion Control—New Environmental Dimension"; pp. 1262-1266; Proceedings of the American Power Conference, date unknown.

M.J. Khesin et al , MPV Combustion Diagnostic and Optimization System, The Mega Symposium; EPRI-DOE-EPA Combined Utility Air Pollutant Control Symposium; Aug. 1999.

GE Brochure "MK Combustion Optimization System." 2001.

Panametrics, Inc. (brochure), In-situ oxygen analyzer FGA411, Sep. 1999.

Nicholas Szabo et al., "Microporous zeolite modified yttria stabilized zirconia sensors for nitric oxide determination in harsh environments," The Ohio State University. 2001.

Eric Wachsman et al. "Selective detection of NOx by differential electrode equilibria", Solid State Ionic Devices II—Ceramic Sensors, Electrochem Soc. Ed 2000-32, 298 304 (2001).

* cited by examiner

METHOD AND APPARATUS FOR MONITORING GASES IN A COMBUSTION SYSTEM

BACKGROUND OF THE INVENTION

The present invention relates to monitoring and measuring gases, such as constituent gases in flue gases in combustion systems, including systems having sensors used in combustion applications, such as boiler, furnace, combustion gas turbine or fossil combustor applications.

To understand the nature and operation of the invention it may be helpful to consider some exemplary applications. For instance, in numerous industrial facilities or environments a hydrocarbon fuel is burned in a combustor (e.g., a boiler or furnace) to produce heat to raise the temperature of a fluid. For the combustor to operate efficiently and to produce an acceptably complete combustion having byproducts/products of combustion that fall within the limits imposed by environmental regulations and design constraints, all of the individual burners should be operating cleanly and efficiently, and all post-flame combustion control systems should be properly balanced and adjusted.

Emissions of unburned carbon, nitric oxides (NO, $NO_2$, NOx), carbon monoxide or other byproducts commonly are monitored to ensure compliance with environmental regulations. As used herein and in the claims, the term nitric oxides shall include nitric oxide (NO), nitrogen dioxide ($NO_2$), and nitrogen oxide (NOx, where NOx is the sum of NO and $NO_2$). The monitoring of emissions heretofore has been done, by necessity, on the aggregate emissions from the combustor (i.e., the entire burner array—taken as a whole). Some emissions, such as the concentration of gaseous combustibles in hot flue gases, are difficult and/or expensive to monitor on-line and continuously. These emissions are typically measured on a periodic or occasional basis. When a particular combustion byproduct is found to be produced at unacceptably high concentrations, the combustor should be adjusted to restore proper operations. However, measurement of aggregate emissions, or measurement of emissions on a periodic or occasional basis, provides little, if any, useful information regarding what particular combustor parameters should be changed to effect such an adjustment.

Three main combustion variables, namely $O_2$, CO and NOx should be continuously monitored to optimize the combustion process and to achieve a goal of providing maximum efficiency at the minimum level of emissions. Solid electrolyte (e.g., zirconia) based combustion sensors are well known and commonly used in fossil combustors to measure oxygen and combustibles (commercial suppliers include Rosemount Analytical, Ametek Thermox, and Yokogawa). These sensors are usually used with reference air applied to one of two electrodes. In most cases the existing sensors are extractive and require high maintenance.

Recently some suppliers have introduced oxygen sensors that do not utilize a continuous supply of reference gas. Instead, these sensors have a sealed internal electrode filled with a mixture of metal/metal oxide that generates a constant partial pressure of O2 inside the sealed volume.

There are a number of methods to measure flue gas combustibles (primarily CO) using solid electrolytes. One of the methods is based on using a fluctuating signal in an in-situ potentiometric solid electrolyte cell directly positioned in the high temperature flue gas stream, as described in U.S. Pat. No. 6,277,268 (Khesin et al.), entitled "System And Method For Monitoring Gaseous Combustibles In Fossil Combustors" (referred to herein as the '268 patent). These sensors are relatively simple in design and provide an immediate response. An example of an existing sensor in production and available on the market is the MK CO sensor manufactured by the General Electric Reuter-Stokes Company of Twinsburg, Ohio.

The '268 patent discloses, among other things, an apparatus for monitoring changes in a concentration of gas molecules of at least a first type in an environment. The apparatus includes a mass of material and first and second electrodes. The mass of material is permeable to ions formed when gas molecules of the first type are ionized. The first and second electrodes are arranged on the mass of material such that, when a concentration of the gas molecules of the first type at the first electrode is different than a concentration of the gas molecules of the first type at the second electrode, gas molecules of the first type are ionized at the first electrode to form ions which flow from the first electrode to the second electrode via the mass of material and are recombined at the second electrode to form gas molecules of the first type, thereby generating a signal between the first and second electrodes. Each of the first and second electrodes is in fluid communication with the environment.

More specifically, the '268 patent discloses a system for monitoring changes in a concentration of oxygen present in an environment, the system includes at least one Nernstian-type gas sensor. The sensor includes a mass of solid-electrolyte material and first and second electrodes. The first and second electrodes are disposed on the mass of solid-electrolyte material to generate a signal therebetween indicative of a difference between an oxygen concentration at the first electrode and an oxygen concentration at the second electrode. Each of the first and second electrodes is in fluid communication with the environment. However, the Nernstian-type gas sensor may be used to monitor the concentration of any number of gases. The mass of material included in the sensor is permeable to ions formed when gas molecules of a first type are ionized. A signal is generated between the at least first and second electrodes in response to changes in the concentration of the gas molecules of the first type in the environment. Further, the sensor may be free of a temperature control device.

The '268 patent further discloses a method for calibrating a gas sensor, the method including supplying each of a first gas having a first profile and a second gas having a second profile, which is different that the first profile, to the gas sensor in a predetermined sequence. The gas sensor or a signal analyzer associated therewith is adjusted based upon an output signal of the gas sensor to calibrate the gas sensor. An apparatus for calibrating a gas sensor includes a switching system and a sequencer. The switching system is in fluid communication with each of a first tank having a first predetermined gas profile and a second tank having a second predetermined gas profile. The sequencer causes the switching system to supply gas from each of the first and second tanks to the gas sensor in a predetermined sequence.

The '268 patent further discloses, such as at FIGS. 8A and 8B, a multi-piece pipe and connector arrangement for assembly and installation of the sensor in a field combustor application.

There are a number of methods to measure NOx in flue gas using Nernstian solid electrolyte sensors in the mixed potential potentiometric mode. In such designs, the analyzed gas, prior to reaching the measuring electrode, passes through a porous filter that enhances its sensitivity to NO or NOx, the sum of NO and $NO_2$. The practical use of such "filtered" NOx sensors is difficult due to the effects of other components, primarily CO and $O_2$.

BRIEF SUMMARY OF THE INVENTION

The present invention overcomes the problems noted above, and offers additional advantages, by providing an improved method and system for monitoring gases in combustion systems. The invention may be used in a number of applications, including power boilers and fossil combustors. In one manner, the invention provides simultaneous monitoring and/or measuring of key combustion components, such as oxygen, NOx and CO, using one solid electrolyte-based in-situ potentiometric sensor. Such sensors can be grouped together to provide necessary profiling and mapping of combustion variables as an effective tool of combustion optimization.

According to one aspect of the present invention, a fluctuational combustibles sensor provides a combined potentiometric $O_2$+CO sensor. In this embodiment, a reference gas (air) is supplied to one electrode (the reference electrode) of the combustibles sensor such that this reference gas flows through the sensor. This may be referred to as a flow-thru $O_2$+CO sensor. The $O_2$ component of the sensor operates like a traditional Nernstian-type sensor in that it is operated in accordance with the Nernst equation. However, the term Nernstian is often used generically to refer to sensors that are a solid electrolyte zirconia-based sensor and that do not operate in accordance with the Nernst equation. The CO and NOx aspects of the sensor are not "Nernstian" in the technical sense. Rather, the CO and NOx sensor configurations of the present invention operate in a mixed potential mode, in that the processing associated with determining concentration of CO and NOx deviates from the Nernst equation based on a number of factors, such as temperature, materials used, etc.

In one manner, the present invention may be used to convert existing sensors or sensor designs, such as the MK CO sensor, into a combined potentiometric $O_2$+CO sensor. This approach offers a less complicated sensor design, where the sensor has a solid electrolyte cell with two measuring electrodes. The in-situ potentiometric sensor generates an output signal which consists of two components, DC and AC. Historically, the DC component has been used to calculate $O_2$ using the Nernst equation and the AC component filtered out of the signal. More recently, the fluctuating AC component has been used to determine concentrations of carbon monoxide (CO), nitric oxide (NOx), or other gaseous combustibles, as described in U.S. Pat. No. 6,277,268. FIGS. 2A and 3A illustrate two exemplary versions of combined $O_2$+CO sensors: a sensor having a solid electrolyte cell with both ends open (FIG. 2A) and a sensor having a solid electrolyte cell with one end closed (FIG. 3A).

When a combustor operates in the balanced-draft mode (under negative pressure), the natural draft can be used as a driving force for a reference air supply. The reference air supply line can also be used for periodic calibration of both $O_2$ and CO sensors by supplying calibration gases to a reference electrode.

Instead of continuous sensor heating and temperature control, the sensor is positioned in the flue gas zone at proper temperature window, for example in many boiler/furnace applications approximately between 900–1500° F. flue gas temperature. The temperature is continuously measured and used to provide compensation. The sensor head is placed inside a protective shell to facilitate its calibration, to reduce the effect of flue gas velocity and to protect its surface from ash deposits.

According to another aspect of the invention, the combustibles sensor is configured or converted into a combined $O_2$+CO sensor, as described above, and additionally configured in combination with a sealed $O_2$ sensor (sealed $O_2$+CO sensor). In this arrangement, a continuous supply of reference gas is not required.

According to another aspect of the invention, the combustibles sensor is configured or converted into a combined potentiometric CO+NOx sensor by using it in combination with a "filtered" NOx sensor. The sensor has one common solid electrolyte cell with two measuring electrodes and one common reference electrode. A porous thin filter made of a material, capable to oxidize CO into $CO_2$ and eliminate the effect of CO, is placed over one of the measuring electrodes. Techniques and materials for filtering CO. This electrode operates in the mixed potential mode and is used to measure NOx. Another measuring electrode operates as a fluctuational CO sensor. As a result, two signals CO+NOx are generated in one potentiometric solid-electrolyte sensor. This sensor arrangement does not require continuous reference gas supply and is essentially as shown in FIG. 4A, except without the reference gas supply. Accordingly, in this embodiment there is no DC component from which to determine $O_2$ concentration.

According to another aspect of the invention, the combined $O_2$+CO sensor, as described above, can be used in combination with the "filtered" NOx sensor to form a combined $O_2$+NOx+CO sensor (FIG. 4A). In this configuration, the sensor has one common solid electrolyte cell with two measuring electrodes and one common reference electrode. One set of electrodes, e.g., the CO electrode in combination with the reference electrode, operates as a Nernstian sensor and is used as a combined $O_2$+CO sensor as described above having DC and fluctuating AC components. Another set of electrodes, e.g., the NOx electrode in combination with the reference electrode and is used to measure NOx, also as described above. As a result, three gas concentrations, $O_2$+NOx+CO, are monitored and measured in one potentiometric solid-electrolyte sensor.

According to yet another aspect of the invention, the in-situ solid-electrolyte sensor, as described above, is equipped with a flexible stainless hose or conduit to facilitate its packaging, assembly, installation and maintenance in a boiler. The actual gas measuring probes could be of significant length, 20–30 feet or more. When the length of the gas measuring probes is significant (exceeds 6–8 feet), the probes have to be assembled onsite, thereby complicating assembly, transportation, insertion and retraction procedures. Using the flexible hose affords greater flexibility associated with onsite installation, in conjunction with a support conduit mounted in the post-flame zone, and allows fabrication of the whole probe to take place at the factory. The unit is then shipped to the site fully assembled and the insertion and retraction of the sensor probe unit is greatly simplified, especially in congested plant environments. FIG. 4A illustrates a gas sensing probe with a flexible hose.

Accordingly, one objective of the present invention is to provide simultaneous and immediate measurements of several key combustion variables, such as the concentration of oxygen, nitric oxides (to include $NO_2$, NO, NOx), and other gaseous combustibles (such as CO), using one solid electrolyte-based in-situ potentiometric sensor. Existing in-situ, solid electrolyte potentiometric combustion sensors allow the measurement of only one combustion variable and have essential operating difficulties. A combustion sensor characterizing several key combustion variables simultaneously and immediately offers significant benefits for successful on-line combustion diagnostics and optimization.

In one manner, the invention improves over known methods by providing enhanced capabilities to simultaneously monitor various gases, for example $O_2$, CO and NOx. One embodiment of the invention provides a supply of reference air to one electrode, an external filter to another electrode, external housing for calibration and flexible hose, in one embodiment made of stainless steel, for more effective assembly, installation and maintenance in combustion applications and environments.

Another object of the invention is to enhance the capabilities of combustibles sensors by combining measurements of several key combustion variables in one in-situ potentiometric solid electrolyte sensor.

Another objective is to convert existing fluctuational combustibles sensor into a combined ($O_2$+CO) sensor either by supplying a reference gas (air) flow to one electrode of the combustibles sensor (reference air sensor) or by using it in combination with a sealed $O_2$ sensor.

Yet another objective of the present invention is to provide a sensor that can be converted into a combined (NOx+CO) sensor by using it in combination with a filtered NO sensor. Further, the sensor can be converted into a combined ($O_2$+NOx+CO) sensor by using it as a flow-thru (or sealed) $O_2$ sensor in combination with a filtered NOx sensor.

It is a further object of the invention to provide an apparatus and system for simultaneously monitoring and measuring concentration levels of flue gas components to minimize undesirable emissions and to optimize combustor operation.

BRIEF DESCRIPTION OF THE DRAWINGS

The present invention can be understood more completely by reading the following Detailed Description of exemplary embodiments, in conjunction with the accompanying drawings, in which.

DETAILED DESCRIPTION OF THE INVENTION

Figure 1A:
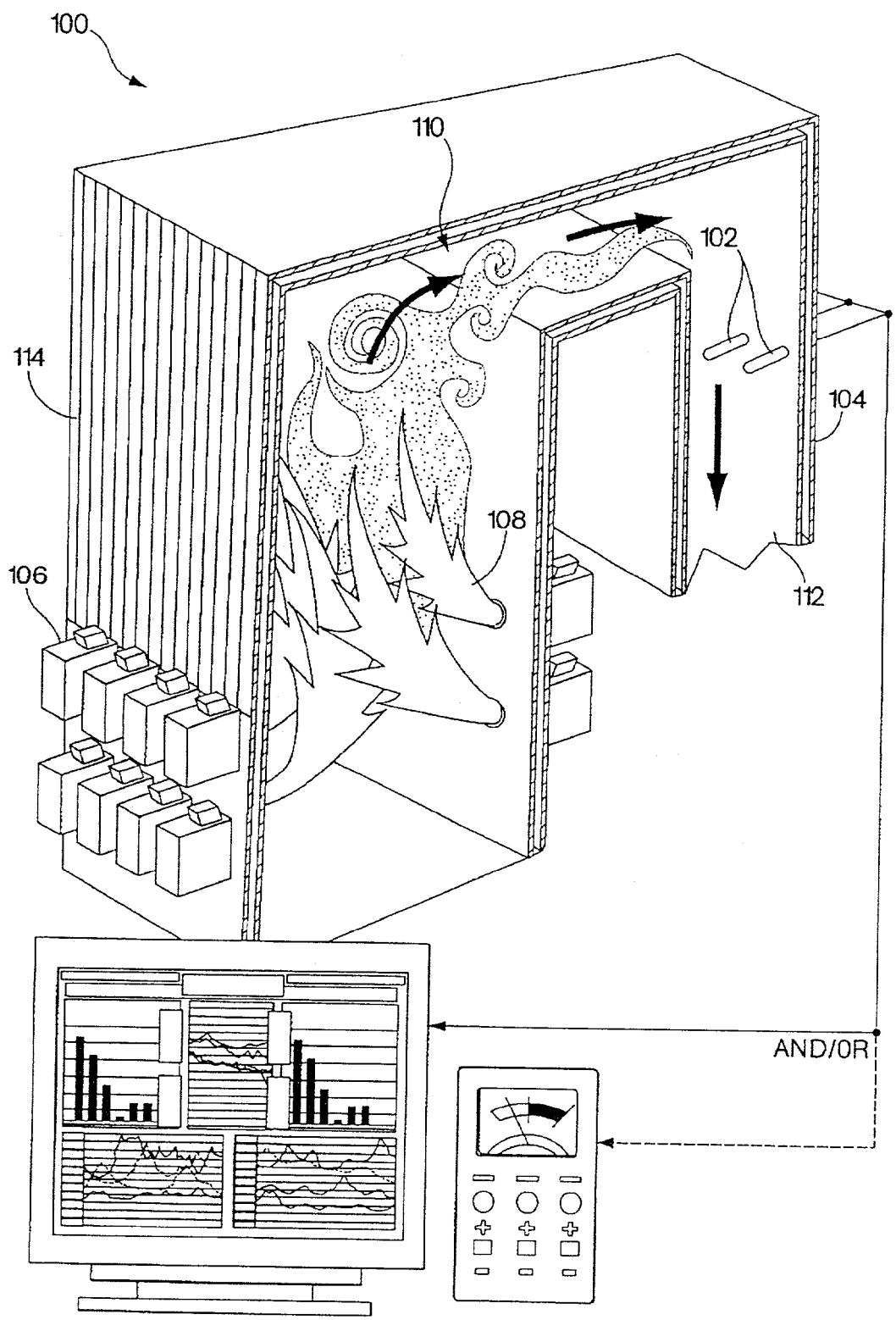
FIGS. 1A and 1B illustrate an example of a boiler having solid-electrolyte sensors embodying the present invention and positioned to produce signals indicative of levels of gaseous combustibles.

The invention may be employed in a number of combustion applications, including power boilers and fossil combustors. In one manner, the invention provides simultaneous monitoring and/or measuring of oxygen, NOx and gaseous combustibles using one common in-situ sensor operating in the potentiometric mode. Such sensors can be grouped together to provide necessary profiling and mapping of combustion variables as an effective tool of combustion optimization.

To achieve the goal of stable and efficient operation of any combustion apparatus, it is useful to achieve continuous, on-line monitoring of various combustion variables and their distribution profiles in different combustion zones. When such monitoring is accomplished effectively, individual burners as well as post-flame combustion controls may be adjusted to achieve optimum relationships between the fuel and air flows, an optimum distribution of individual air flows and reburning fuel flows, and an optimization of other boiler adjustments, thereby increasing the efficiency of the combustor significantly.

It is known to employ an in-situ oxygen sensor to monitor the concentration of oxygen in a combustor. Typically, such a sensor employs a pair of porous metal (e.g., platinum) electrodes disposed adjacent one another on opposite sides of a solid electrolyte (e.g., yttria ($Y_2O_3$) stabilized zirconia ($ZrO_2$) (YSZ)) element, with one of the electrodes (a reference electrode) being surrounded by a gas having a predetermined oxygen concentration, and the other electrode (a sensing electrode) being exposed to the gas being monitored. In these sensors, when the solid electrolyte element is heated to a sufficient temperature (e.g., above 600° C.), it becomes permeable to oxygen ions. Therefore, when the concentration of oxygen molecules is greater at one of the electrodes than at the other, oxygen ions will migrate from one of the electrodes to the other, with the electrodes serving as catalytic surfaces that enable oxygen molecules to become oxygen ions. The electron imbalance resulting from this flow of oxygen ions and the ionization/deionization occurring at the respective electrodes generates a voltage between the electrodes that is a function of the ratio of the partial pressures of oxygen at the two electrodes, as well as the temperature of the solid electrolyte material. The voltage generated between the two electrodes is defined by the so-called "Nernst" equation, as follows:

$$E=(RT/4F) \times L_n(P1/P2)+C$$

wherein:
E=the voltage out;
T=the absolute temperature of the sensor;
R=the Universal Gas Constant;
F=Faraday's Constant;
P1=the partial pressure of oxygen in the reference gas;
P2=the partial pressure of oxygen in the monitored gas;
C=a constant for each individual sensor, and
Ln(P1/P2) is the natural logarithm of the ratio P1/P2.

As can be noted, the only variables in the Nernst equation are E, T, P1, and P2. When the partial pressure of oxygen in the reference gas (P1) is held constant, the signal E output by such a prior art sensor is therefore affected only by: (1) changes in the partial pressure of oxygen in the measured gas P2, and (2) changes in the temperature T of the sensor. By eliminating the effect of the sensor's temperature T on the value of the voltage E, the voltage E output by such a sensor responds only to changes in the value P2 and can therefore be used as an accurate indicator of the concentration of oxygen in the measured gas (i.e., E=f(P2)). The effect of a Nernstian-type gas sensor's temperature T on the value of the voltage E output therefrom is typically eliminated using one of two techniques. According to one technique, a heater is provided within the sensor, and is the heater activated selectively to maintain the sensor at a constant temperature T. In accordance with another technique, a thermocouple is disposed within the sensor to measure the sensor's temperature T, and the voltage E is adjusted to compensate for changes in the temperature T. As used herein, the term "temperature control device" refers to any device, circuitry, hardware, software, or any combination thereof, that is employed to eliminate the effect of the temperature T of a Nernstian-type gas sensor on the voltage E output thereby, using either of the two above-described techniques.

With Nernstian-type gas sensors that employ at least one porous catalytic electrode (e.g., a porous platinum electrode), when gaseous combustibles come into contact with the catalytic electrode under proper conditions, they are caused to combine chemically with oxygen in a combustion-type reaction to form non-combustible by-products. For example, two carbon monoxide molecules ($2CO$) may combine with one oxygen molecule ($O_2$) to form two carbon dioxide molecules ($2CO_2$) (i.e., $2CO+O_2=2CO_2$), or two hydrogen molecules ($2H_2$) may combine with one oxygen molecule ($O_2$) at the electrode to form two water molecules ($2H_2O$) (i.e., $2H_2+O_2=2H_2O$). As used herein, the term "gaseous combustible" refers to any gaseous molecule that is capable of being combined chemically with oxygen in a combustion-type reaction. Because of this chemical reaction between gaseous combustibles and oxygen at the catalytic electrode, a rise in the level of gaseous combustibles causes additional oxygen molecules near the electrode to be consumed, thereby decreasing the concentration of oxygen at the electrode and correspondingly changing the voltage output by the sensor. Similarly, a decrease in the level of gaseous combustibles near the electrode causes fewer oxygen molecules near the electrode to be consumed, thereby increasing the concentration of oxygen at the electrode and correspondingly changing the voltage output by the sensor.

In the flue gas in the post flame zone (explained below) of a combustor, carbon monoxide (CO) is typically the most prevalent gaseous combustible present. In fact, carbon monoxide typically accounts for more than ninety-five percent of the gaseous combustibles present in the flue gas. Therefore, the output signal from a Nernstian-type gas sensor sensing the flue gas of combustor may serve as a reliable indicator of the level of CO present therein.

Signals from Nernstian-type gas sensors include two components: (1) intensity ("the DC component"), and (2) fluctuating frequency ("the AC component"). The DC component, according to the Nernst equation, is a function of several parameters, including sensor temperature and oxygen concentration in the analyzed and reference gases. The DC component has been the component of interest in systems employing these sensors for determining $O_2$ concentration. The fluctuating AC component is commonly filtered from the output signal of an oxygen sensor because it is considered to be useless noise. In non-in-situ sensors, such as extractive arrangements in which the sensor element is external to the post-flame zone area and sample flue gas is extracted and delivered to the external sensor, delays are introduced and the accuracy of the fluctuating AC component is significantly impaired and in many instances effectively lost. Accordingly, the fluctuating component has been typically considered of little use in such systems.

Experimental testing of boilers, supported by theoretical analysis, has demonstrated that the fluctuational AC component of an in-situ oxygen sensor may be used as an indicator of combustion efficiency. This topic is discussed, for example, in two articles: (1) Khesin, M. J., Johnson A. J., "Combustion Control: New Environmental Dimension," American Power Conference, Chicago, 1993; and (2) Khesin, M. J., Ivantotov, A. A., "Fluctuations of Flue Gas Oxygen as Indicator of Combustibles," Teploenetgetika, 1978, 5, each of which is hereby incorporated herein by reference. As discussed in these articles, an output signal generated by a solid-electrolyte, in-situ oxygen sensor can be used to monitor gaseous combustibles by correlating the fluctuating AC component of such a signal with gaseous combustibles.

In order to exploit the phenomenon described in references (1) and (2) referenced immediately above in a practical and useful manner, however, serious technical difficulties needed to be overcome. These difficulties include high operating temperatures (e.g., above eight-hundred degrees Celsius (° C.)), gradual reduction of the catalytic capacity of sensor electrodes, inconsistency of results, and uncertainty of signal processing algorithms used to obtain such results. The present invention overcomes these difficulties by providing an improved and more versatile sensor design, and an effective and universal method and system for monitoring gaseous combustibles in a combustor.

In one application of the present invention, one or more solid-electrolyte gas sensors 102 are positioned in the flue gas flow in the post-flame zone (described below in connection with FIG. 1A) of a combustor 100 to measure fluctuations in the oxygen concentration of the flue gas. The fluctuations measured by these sensors may be used to calculate values which correlate with real-time levels of gaseous combustibles.

In one embodiment of the invention, each sensor includes a solid-electrolyte (e.g., YSZ) element and at least two metal, preferably porous, (e.g., platinum) electrodes associated therewith. In accordance with an aspect of the present invention, at least one of the electrodes is in fluid communication with a flue gas for monitoring constituent gas molecules in the flue gas. At least one other electrode is isolated so as not to be in direct fluid contact with the flue gas and may be immersed in a reference gas. The gas to be monitored may be for instance oxygen, CO, NOx, or other combustible gases. By way of example, the electrode isolated from the flue gas is immersed in a reference gas, e.g., air. And say that the other electrode is in communication with the flue gas and is connected to a system for monitoring the concentration of oxygen or determining the concentration of some other gas based on the concentration of oxygen. In this manner, when the oxygen concentration in the flue gas changes from a first level to a second level, the rate at which the oxygen concentration at the flue gas electrode changes from the first level to the second level is different than the rate, if it changes at all, at which the oxygen concentration at the isolated electrode changes from the first level to the second level. In other words, each of the electrodes may be configured and arranged so that there is a time constant associated therewith that determines how quickly the oxygen concentration level at that electrode rises or falls to a new oxygen concentration level in the flue gas and isolated reference environments.

Any of a number of different relationships involving a time constant may exist between the oxygen concentration at each electrode and the oxygen concentration in the respective environments, and the invention is not limited to any particular type of relationship. One example of a relationship between the oxygen concentration at an electrode and the oxygen concentration in the respective environment is an exponential relationship involving a time constant Tc, such as:

$$C_E = C_C + \Delta C_C * (1 - e^{-t/Tc}),$$

wherein:

$C_E$=the concentration of oxygen at the electrode,
$C_C$=the concentration of oxygen in the environment,
$\Delta C_C$=the change in concentration of oxygen in the environment,
e=the exponential operator,
t=the time elapsed since the change in oxygen concentration occurred, and
Tc is a time constant specific to the electrode.

The electrodes are in fluid communication with their respective environments by different "degrees" when the time constants $T_C$ of the two electrodes are different. The electrodes may be configured and/or arranged in any of numerous ways so that their time constants $T_C$ differ from one another, and the invention is not limited to any particular technique for accomplishing the same. In various illustrative embodiments, for example, this goal may be achieved simply by employing electrodes that differ in their design, material and/or characteristics. For example, the electrodes may have different geometries, may be coated by materials having different porosities, may be coated by different materials, and/or may be coated by different amounts of a material, e.g., a porous, high-temperature epoxy.

When the electrodes are configured and arranged so as to have different time constants, a measured potential between the electrodes represents primarily the fluctuational AC component of the oxygen concentration in the measured gas, rather than representing both the AC and DC components, or primarily the DC component, as was done with the prior art sensors described above in which one of a pair of sensors was surrounded by a gas having a predetermined oxygen concentration. What constitutes a suitable difference between the time constants of the electrodes may vary from application to application, and the invention is not limited to any particular difference between the time constants. In various embodiments, for example, the time constants of the electrodes may differ from one another by some value between a few (e.g., two) milliseconds and several (e.g., ten) minutes.

It should be appreciated that the novel sensor configuration described herein is not limited to applications wherein the concentration of oxygen is monitored, as this sensor may also find applications in sensing the concentration of numerous other types of gases, e.g., carbon monoxide (CO), nitric oxide (NOx), etc., as well.

In one embodiment of the invention, the output signal from an in-situ oxygen sensor is fed to a signal analyzer, e.g., a programmed computer, where it is analyzed and used to generate one or more combustion parameters that are correlated with combustion conditions.

In one manner, the sensor output signals are analyzed to correlate an output range with a known gas concentration. For example, in a particular application and particular fuel, the NOx range of particular interest may be from 0–500 ppm (parts per million) NOx. From this, a response curve can be established by exposing the sensor to known quantities of NOx and mapping the measured output voltage response (such as in mVolts) with the known NOx concentration. Similarly, for a range of oxygen of 0–10%, the sensor may be exposed to known concentrations of oxygen and the resulting voltage response curve is applied in processing the signals received in the intended application. Likewise, for a CO range of 0–1000 ppm, a voltage response curve is established and applied in processing measured concentrations in intended applications. Although preferably sensors made pursuant to a given design will behave essentially the same, some adjustment or offset may be required, onsite or offsite, to "tweak" or otherwise bring a particular sensor into compliance with the design response curve. Although some examples of gas concentration ranges are provided, the ranges are largely dependent upon the particular combustor application or design, mode of operation and the particular fuel(s) used.

In one embodiment, the output signal is processed in the frequency domain by using a frequency domain amplitude spectrum of the signal to generate an extremum function (as described below), and one or more combustion parameters are calculated based upon one or more characteristics of the extremum function so generated. In another embodiment, the signal is processed in the time domain (as described below) by analyzing one or more characteristics of a time domain representation of the signal during a selected time interval. In still another embodiment, the signal is processed both in the frequency and time domains, and the results of calculations in each domain are combined to yield one or more combustion parameters. The levels of the gaseous combustibles may then be estimated using a combination of these calculated combustion parameters, along with limiting conditions which may depend, for example, on the temperature, level of oxygen, and/or combustibles in the controlled gas. These limiting conditions may, for example, be determined from the DC component of the sensor signal. It should be appreciated that this aspect of the invention relating to novel techniques for processing signal(s) from oxygen sensor(s) in the frequency and/or time domains to yield combustion parameters may be employed either with the prior art oxygen sensors described above which surround one electrode with a reference gas, with the oxygen sensors described above in which at least two electrodes are each in fluid communication with a common gaseous environment, or with any other type of sensor which generates a signal that includes a fluctuational AC component representing a concentration of a gas (e.g., oxygen) or other fluid.

When a single sensor is used, it generates a signal indicative of the level of gaseous combustibles at the particular point where the analyzed gas comes in contact with the sensor. The signal from such a single sensor may provide a sufficient amount of information to permit the operation of a small, single-burner industrial combustor to be optimized. When several sensors are inserted into the flue gas flow (e.g., across the width) of a combustor, the outputs of the sensors represent a distribution profile of the gaseous combustibles within the combustor. Such a profile can be utilized for combustor balancing and optimization. For example, individual burners and/or post-flame combustion systems can be adjusted to alter the generated profile until it reflects that optimal and balanced combustion conditions have been achieved. An understanding of (1) how the profile should appear when such optimal and balanced combustion conditions have been achieved, and (2) how individual burners and/or post-flame combustion systems affect different aspects of the profile may be obtained through empirical measurements. This boiler balancing and optimization may be particularly useful for larger, multi-burner combustion systems.

Figure 1B:
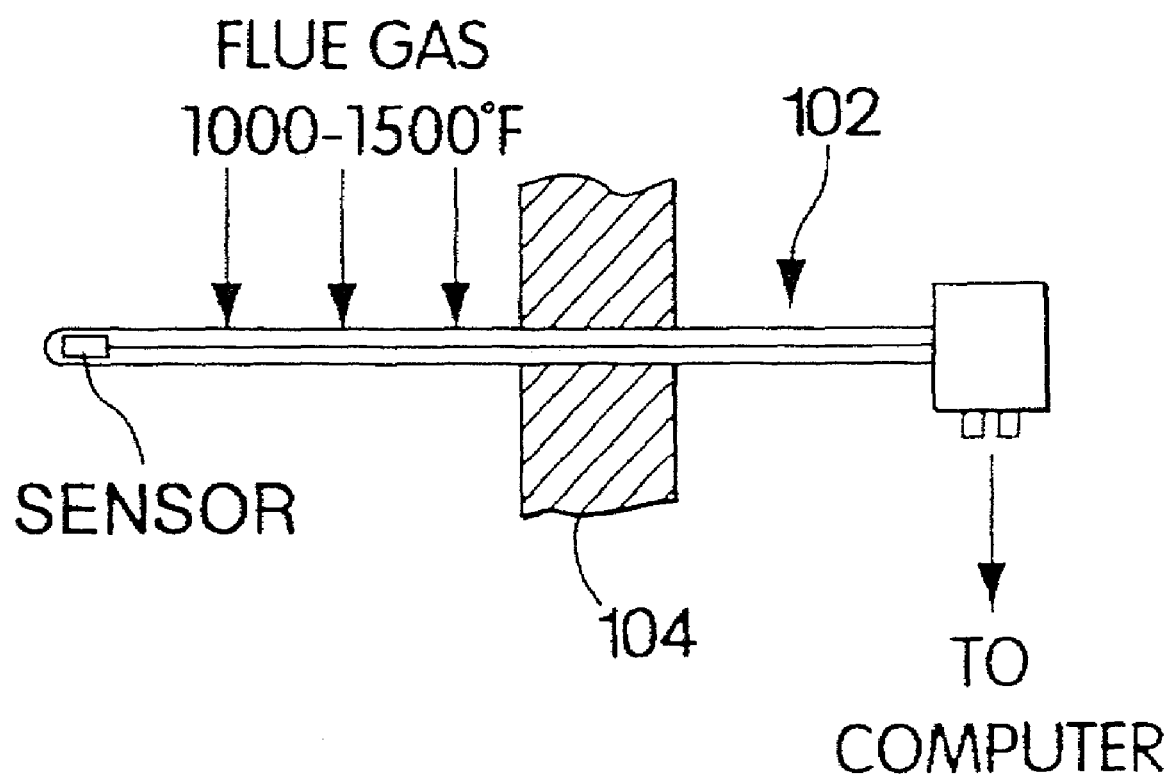

With reference to FIGS. 1A and 1B, there is shown a cross-sectional illustration of a combustor 100 and typical sighting of several in-situ oxygen sensors 102 positioned across the width of a post-flame, flue gas duct 104 of the combustor 100 to monitor the stream of hot flue gases flowing therethrough in a post-flame zone. The sensors 102 may, for example, be solid-electrolyte sensors which measure the concentration of (and/or changes in the concentration of) oxygen in the flue gases, or any other sensors capable of generating a signal indicative of the concentration of (and/or changes in the concentration of) one or more other types of gases present in the flue gases. In practice, any number of sensors 102 may be installed (preferably in a row) across the width of the flue gas duct 104. The sensors may also be arranged in a vertically-oriented row, or in a grid-like manner or other effective pattern and may extend varying depths into the duct to monitor the distribution profile of gaseous combustibles.

In some embodiments, the combustor 100 may be more than one, two or even three hundred feet tall. As shown in FIG. 1A, the combustor 100 may include a plurality of combustion devices (e.g., combustion device 106) which mix fuel and air to generate flame in a flame envelope 108 within the combustor 100. The combustion devices may be any of numerous types of flame-producing devices, and the invention is not limited to a particular type of combustion device. According to one embodiment, for example, the combustion devices may include burners (e.g., gas-fired burners, coal-fired burners, oil-fired burners, etc.). In such an embodiment, the burners may be arranged in any manner, and the invention is not limited to any particular arrangement. For example, the burners may be situated in a wall-fired, opposite-fired, tangential-fired, or cyclone arrangement, and may be arranged to generate a plurality of distinct flames, a common fireball, or any combination thereof. Alternatively, a combustion device called a "stoker" which contains a traveling or vibrating grate may be employed to generate flame within the combustor 100.

As defined in a publication by the National Fire Protection Association (NFPA) of Quincy, Mass., entitled "NFPA 85C, an American National Standard," p. 85C-11, Aug. 6, 1991, "flame" refers to "the visible or other physical evidence of the chemical process of rapidly converting fuel and air into products of combustion," and a "flame envelope" refers to "the confines (not necessarily visible) of an independent process converting fuel and air into products of combustion."

Referring to FIG. 1A, when the combustion devices 106 in the combustor 100 are actively burning fuel, two distinct locations can be identified within the combustor 100: (1) a flame envelope 108, and (2) a so-called "post-flame" zone 110, which is the zone outside of the flame envelope 108 spanning some distance toward the exit 112. Outside the flame envelope 108, hot combustion gases and combustion products may be turbulently thrust about. These hot combustion gases and products, collectively called "flue gas," make their way away from the flame envelope 108 toward an exit 112 of the combustor 100. Water or another fluid (not shown) may flow through the walls (e.g., wall 114) of the combustor 100 where it may be heated, converted to steam, and used to generate energy, for example, to drive a turbine. In the embodiment shown, the sensors 102 are located in the post-flame zone 110 of the combustor 100. It should be appreciated, however, that the invention is not limited in this respect, and that the sensors 102 alternatively may be disposed in the flame envelope 108 if constructed to withstand the harsh, high-temperature environment thereof.

As mentioned above, in one embodiment of the invention, a voltage difference across the sensor and reference electrodes includes a fluctuational component that may be analyzed to measure the concentrations of gaseous combustibles. The reason for this correlation is believed to be as follows. Individual burner flames comprise a multitude of eddies of various sizes inside and around the flame envelope 108. These eddies contribute to generating the familiar flame flicker at various frequencies as a result of turbulent mixing at the edges of the fuel and air jets. The eddies are transformed in the combustion process, and move in the general direction of the furnace exit 112. The overall combustion turbulence reflects the process of energy transfer from large-scale eddies to smaller and smaller eddies, down to the molecular level. The rate of the mixing process and the resulting intensity of these turbulent activities determines combustion stability and directly relates to the processes of formation and destruction of gaseous combustibles. Most of these chaotic, turbulent activities begin and occur in the flame envelope 108.

Some turbulent activities do take place in the flue gas flow of the post-flame zone 110. However, small eddies associated with combustion kinetics (i.e., small-scale, high-frequency turbulence) tend to dissipate quickly and generally do not reach the post-flame zone 110. Typically, only large eddies (i.e., large-scale, low frequency turbulence) are present in the post-flame zone 110. This low-frequency turbulence reflects combustion variables (e.g., an amount of unburned carbon and other combustibles), particularly those associated with the secondary combustion processes that are influenced by post-flame combustion control systems, such as overfire air and reburning. A turbulent stream of hot flue gases passing into the flue gas duct 104 carries products of incomplete combustion, including gaseous combustibles. As mentioned above, these gaseous combustibles travel in the turbulent flue gas flow as relatively large eddies. And such eddies, containing gaseous combustibles, should contain a very low concentration of oxygen. Each time the proper conditions occur, such as the presence of a catalyst and a high temperature (e.g., between 900 and 1500° F.) near a sensor 102, the gaseous combustibles are caused to burn and the oxygen concentration near the sensor is reduced. These fluctuations in the oxygen concentration near the sensor's electrode(s) cause pulses to be generated in the signal output by the sensor 102. The frequency and amplitude of these pulses characterizes the level of gaseous combustibles present in the analyzed flue gas flow.

The relationship between the sensor output signal and levels of gaseous combustibles may be affected by various factors, including operating combustion parameters, physical parameters, and chemical reactions. In order to more accurately monitor this multi-variable process, according to one embodiment of the invention, two or more mathematically different signal processing algorithms are employed simultaneously to analyze the signal output by the sensor, and the results of the several algorithms are combined.

Examples of methods and algorithms for processing information and signals received from gas sensors of the type described above are described, for example, in U.S. Pat. No. 6,277,268, which is hereby incorporated herein by reference in its entirety. The '268 patent discloses signal processing systems and calculations, such as conducted in the time and frequency domains, that are applicable for use with the sensor embodiments described herein. It is understood, however, that the gas sensor of the present invention is not limited to use in the processing systems described herein or in the '268 patent, but may be used in any system adapted to realize and appreciate the information obtainable from the beneficial use of the inventive gas sensor.

Figure 2A:
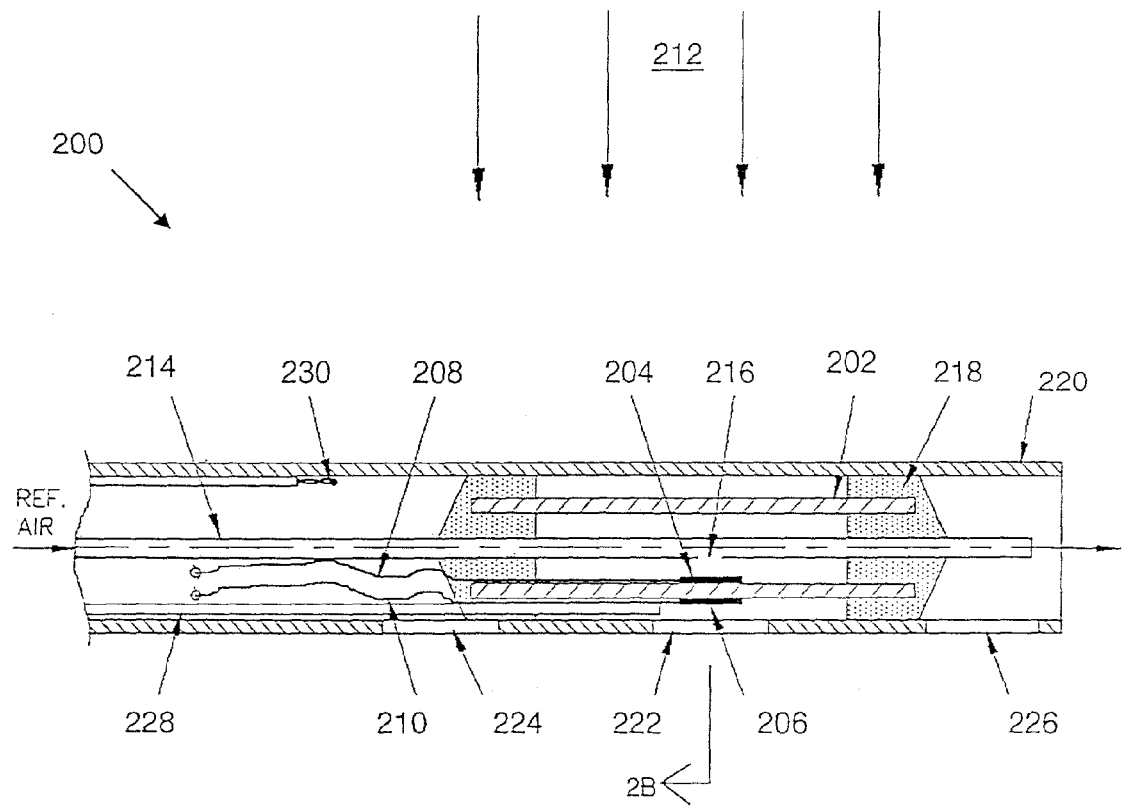
FIGS. 2A and 2B are sectional views of a gas-sensing probe incorporating a first embodiment of the present invention, specifically an oxygen/combustibles sensor with one set of electrodes.
Figure 2B:
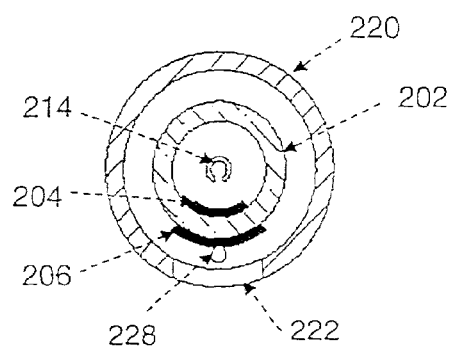

Referring now to the exemplary gas sensor embodiments of the figures, which are provided by way of example and not limitation, FIGS. 2A and 2B illustrate in sectional view a sensor element 200 incorporating the present invention for use in combustion systems. Specifically, a combined $O_2$+CO sensor 200 is arranged as follows. A solid electrolyte (e.g., zirconia) cell 202 has one set of electrodes with internal electrode 204 and external electrode 206 and the corresponding leads 208 and 210. The cell is placed in the stream of the process gas 212 at the required high temperature condition (usually in the 900–1500° F. range) which is provided by the analyzed gas itself or by an additional heater or other source. In one arrangement, cell 202 is made in the form of an open tube. A smaller tube 214 is connected to a supply of reference gas (e.g. air) and supplies the reference gas to the cell (if open ended) the reference gas conduit passes through the cell and the reference gas (air) flows through cell 202. This version is called a "flow-thru" sensor. Tube 214 is preferably made of a material having a coefficient of thermal expansion compatible with the solid electrolyte material of cell 202. This tube has an opening 216 inside to provide a constant concentration Of $O_2$ inside the sensing chamber formed in the cell. The gap between the internal tube 214 and the cell 202 should be thoroughly sealed at the ends of the cell by a high temperature seal, sealing ring or sealing adhesive 218, this seal must also be compatible with regard to thermal expansion of the sensor.

When measuring a constituent gas, for example oxygen, even a small leak in and out the cell may be detrimental to the sensor operation; for instance, it may significantly distort the $O_2$ measurement results. That is why it is important to make sure that (a) the internal tube is sealed properly; and (b) the sensor is designed to prevent the effects of the potential leakage on measurement results. In measuring $O_2$, the processing as described herein above using the Nernst equation is in order. For measuring CO, the general method described above and in the '268 patent may be used. The CO concentration may be analyzed using time domain and/or frequency domain. It should be appreciated that the selected form of processing the fluctuational component to determine CO concentration may depend upon several factors, such as the type of combustor, the fuel type, and the desired or required level of accuracy. In certain situations, such as in the case of simplified combustors or where a high level of accuracy or sensitivity in CO measurement is not required, a simplified processing may be acceptable, for instance calculating the standard deviation of the signal fluctuations (the AC component).

The in-situ sensor has several design features. In one embodiment, Cell 202 is made sufficiently long (for example up to 3–5 inches long) and the electrodes 204 and 206 are positioned in its middle section (approx. ¼ of the total length). The end sections of the cell are preferably not covered by the electrodes to provide more effective air-tight sealing and also to create conditions that, even if a leak occurs, it will be carried away by the stream of the analyzed process gas. For this purpose, the sensor is placed into an external housing 220 with, in one embodiment, three openings: central opening 222 to provide access of the process gas to the external electrode 206 and end openings 224 and 226 to create an additional draft for potential leaks. The sectional view of FIG. 2B is taken across the openings 216 and 222 and electrodes 204 and 206. To prevent erosion and deposits, openings 222–226 should be pointed away from the incoming flue gas flow. It is also important that the sealing material 218 does not come in contact with the porous electrodes (for example made of platinum).

Additional tube 228 is provided inside housing 220 for calibration purposes. A calibration gas with a fixed concentration of $O_2$ can be supplied from outside to the external electrode 206, or a sample of the analyzed gas can be drawn out to a reference gas analyzer. Thermocouple 230 is positioned in close proximity to the cell 202 to be used for temperature monitoring, control and/or compensation.

Figure 3A:
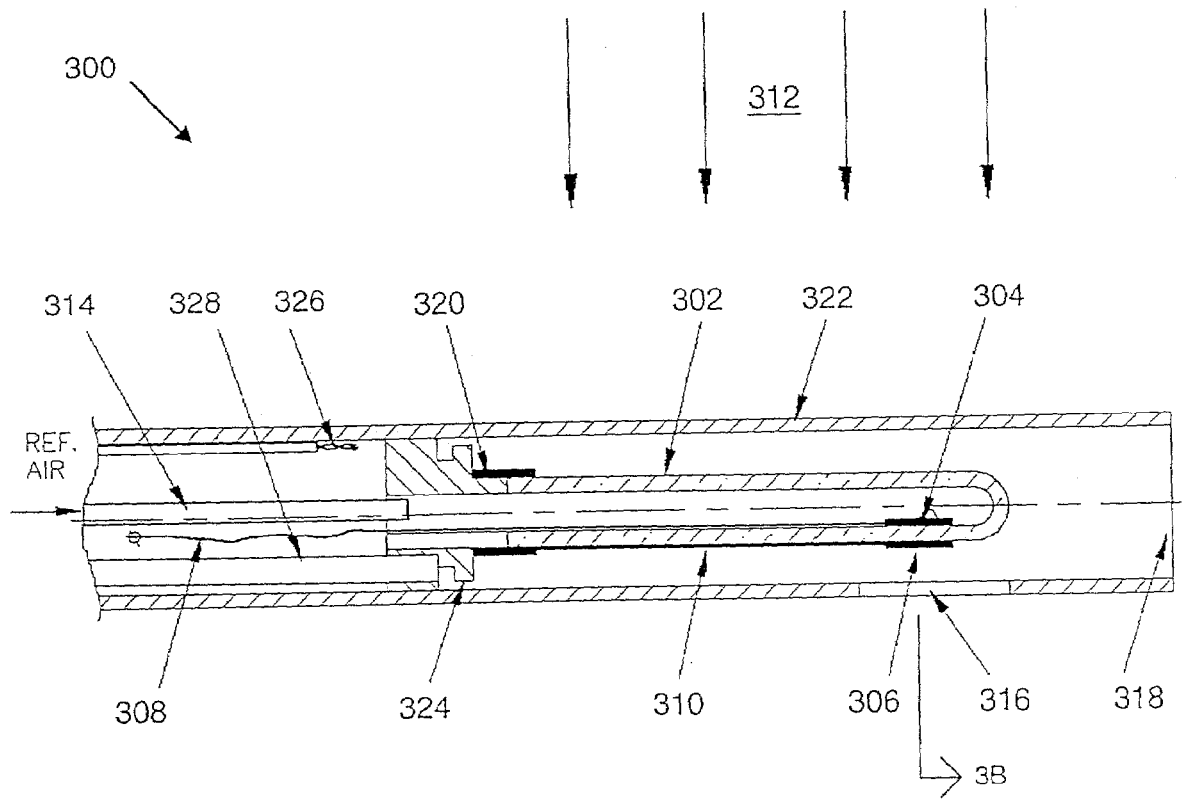
FIGS. 3A and 3B are sectional views illustrating a second embodiment of the invention, specifically an oxygen/combustibles sensor with one set of electrodes (one end closed)
Figure 3B:
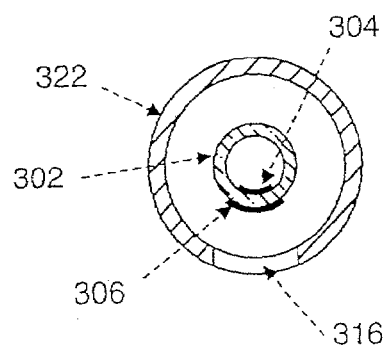

Now referring to the sectional views of FIGS. 3A and 3B, which illustrate a second embodiment of a combined $O_2$+CO gas sensor 300 incorporating the present invention, the solid electrolyte cell 302 has one end closed and has a similar set of electrodes: internal electrode 304 and external electrode 306 with the corresponding leads 308 and 310. The cell is placed in the process gas stream 312 at the required high temperature conditions. In this arrangement reference gas (air) is supplied through tube 314. Protective sleeve 322 may have a side opening 316 or end opening 318 to allow the process gas to reach the external electrode 306. Solid electrolyte cell 302 is mounted and bonded to a metal element 320 which is brazed to adapter 324. Mount 320 also provides an electrical connection with the external lead 310.

Mount 320 is made of a material with a coefficient of thermal expansion compatible with the material of cell 302. Reference gas (air) is supplied via tube 314 to inside of cell 302 and escapes back through the protective sleeve 322. Cell 302 is mounted in the protective sleeve 322 and sealed by means of adapter 324.

An additional tube 328 is provided inside the assembly for calibration purposes. A calibration gas with a fixed concentration of $O_2$+CO can be supplied to the external electrode 306 of cell 302, or a sample of the analyzed process gas can be drawn out to a reference gas analyzer. The sectional view of FIG. 3B is taken across the opening 316 and electrodes 304 and 306. Thermocouple 326 is positioned in close proximity to the measuring cell to be used for temperature monitoring, control or compensation.

According to another aspect of the invention, the combustibles sensor is configured or converted into a combined $O_2$+CO sensor using a sealed $O_2$ sensor (sealed $O_2$+CO sensor). An example of a sealed $O_2$ sensor is model FGA411 manufactured by Panametrics, Inc. of Waltham, Mass. Such a sealed $O_2$ sensor does not require the use of a reference gas. In this case the sensor design may be essentially the same as that of FIG. 3A, only without the reference air supply and with the electrode sealed off and surrounded by a media or material to effect an internal-reference sensor.

According to another aspect of the invention, the combustibles sensor can be configured or converted into a combined CO+NOx sensor by using it in combination with a "filtered" NOx sensor. The sensor has one common solid electrolyte cell with two measuring electrodes and one common reference electrode. A porous thin filter made of material suitable to oxidize CO into $CO_2$ to eliminate the effect of CO, is placed over one of the measuring electrodes. This electrode operates in the mixed potential mode and is used to measure NOx. Examples of operation in the mixed potential mode and of filter devices for use in NOx analysis are described in the following references, which are incorporated herein by reference: Nicholas Szabo et al. "Microporous Zeolite Modified Yttria Stabilized Zirconia Sensors For Nitric Oxide Determination In Harsh Environments", The Ohio State University, 2001, and Eric Wachsman et al., "Selective Detection Of NOx By Differential Electrode Equilibria", Solid State Ionic Devices II—Ceramic Sensors, Electrochem. Soc., Ed., 2000–32, 298–304 (2001). Another measuring electrode operates as a fluctuational CO sensor, as described above. As a result, two signals, CO+NOx, are generated in one potentiometric solid-electrolyte sensor. In this arrangement, the sensor does not require a continuous reference air supply.

Figure 4A:
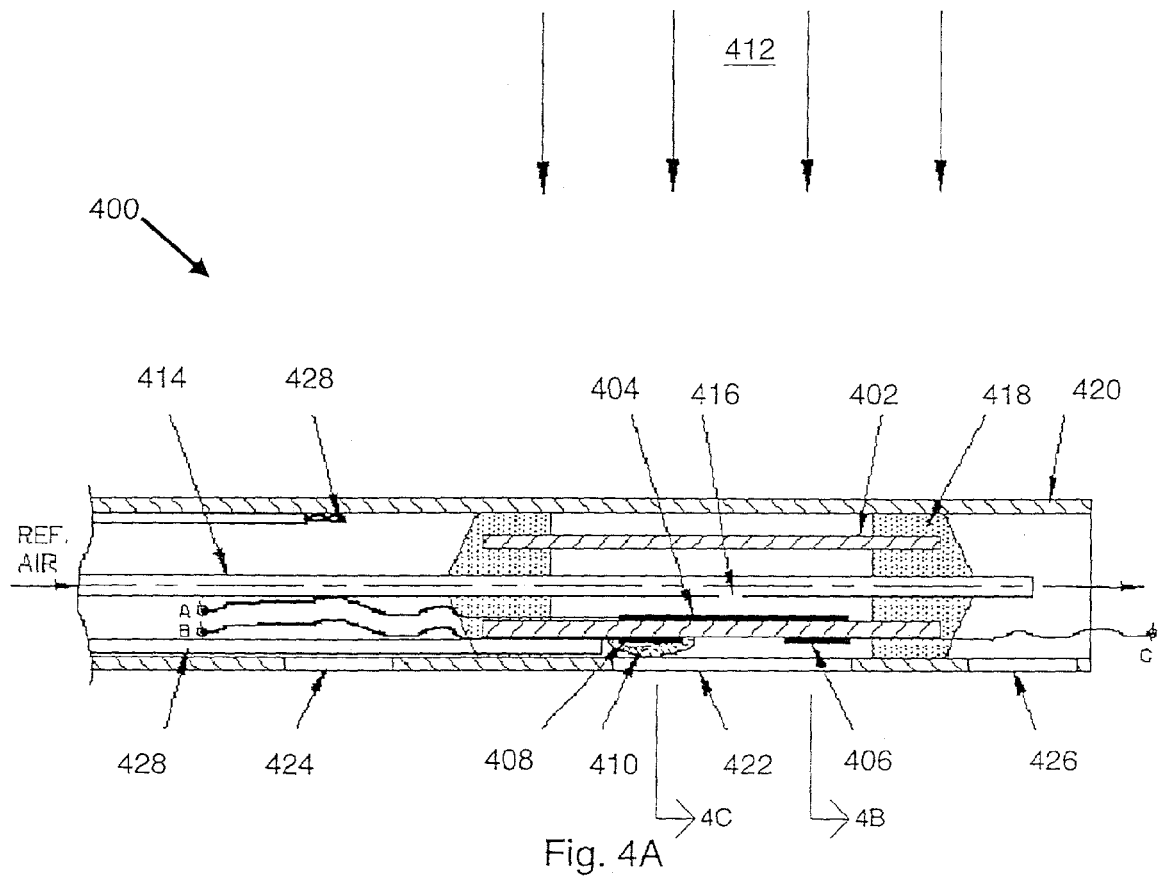
FIGS. 4A, 4B and 4C are sectional views illustrating a third embodiment of the present invention, specifically a combined $O_2$+NOx+CO sensor with two sets of electrodes.
Figure 4C:
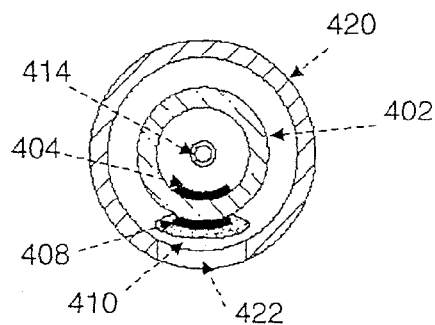
Figure 4B:
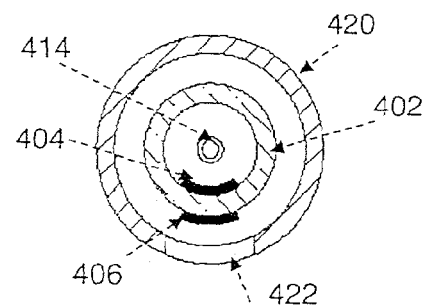

According to another aspect of the invention, the combined $O_2$+CO sensor, described above, can be converted into a combined $O_2$+NOx+CO sensor by using it in combination with a "filtered" NOx sensor, described above. A "flow-thru"

version of such sensor is schematically shown in FIGS. 4A and 4B. Sensor 400 includes a cell 402 that has two sets of electrodes: one common reference electrode 404 and two measuring electrodes 406 and 408 with the corresponding connecting leads A, B and C. A reference gas, e.g., air, is delivered to the sealed space surrounding electrode 404 via opening 416 in supply tube 414. The space is defined in part by cell 402 and is insulated by high temperature seal or sealant 418, similar to that shown in FIG. 2A. The sectional view of FIG. 4B is taken across electrodes 404 and 406.

A porous thin filter 410 made of a material, capable to oxidize and practically eliminate the effect of CO, e.g., as described in the references incorporated above, is placed over measuring electrode 408. The sectional view of FIG. 4C is taken across electrodes 404, 408 and filter 410. This electrode operates in the mixed potential mode and is used to measure NOx. Another measuring electrode operates as a Nernstian sensor and is used as a combined $O_2$+CO sensor, as described and illustrated in FIG. 2A and above. This sensor will require a continuous reference air supply. As a result, all three signals $O_2$+NOx+CO are generated in one potentiometric solid-electrolyte sensor.

For NOx determination, the sensor should be pre-calibrated based on the relationship between the voltage measured from the filtered electrode and the known NOx concentration to establish an expected response curve, in a manner such as described above, to cover a NOx concentration range determined to be appropriate for the particular design or application. A particular sensor and processing function may be further calibrated, onsite or offsite, by exposing the particular sensor to a known NOx concentration and adjusting the sensor response to more closely align with the expected or design response curve.

Figure 5:
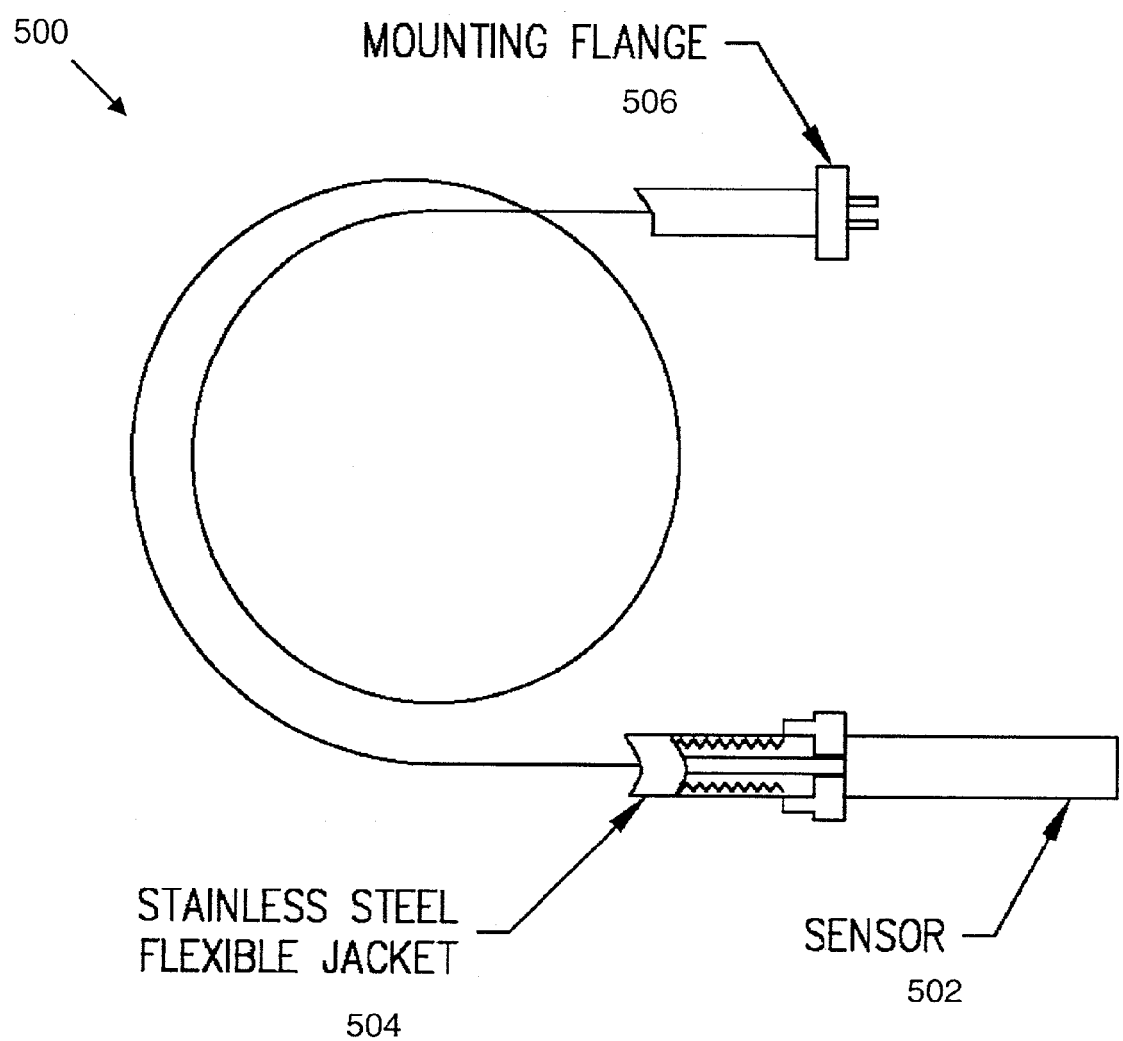
FIG. 5 illustrates an inventive gas sensing probe having a flexible component for enhanced assembly and installation.

According to yet another aspect of the invention, the in-situ solid electrolyte sensor 502 is equipped with a flexible stainless hose or jacket 504 to facilitate its packaging, assembly, installation and maintenance in a boiler, as illustrated in FIG. 5. Existing in-situ combustion sensors could be of significant length, 20–30 ft or more. These sensors have traditionally been assembled at site, and their assembly, transportation, insertion and retraction is difficult. Use of the flexible hose enables complete assembly and testing of the sensor at the factory. On site the sensor can be easily assembled and inserted into a permanent support tube. The risk of damage during field assembly is eliminated, removal and replacement is simplified. The overall weight of the sensor is reduced by over thirty percent. The flexible arrangement also provides ease in installing and retrofitting sensors in locations that are difficult to access physically, such as where sensors are located at confined spaces.

While the foregoing description includes many details and specificities, it is to be understood that these have been included for purposes of explanation only, and are not to be interpreted as limitations of the present invention. Many modifications to the embodiments described above can be made without departing from the spirit and scope of the invention, as is intended to be encompassed by the following claims and their legal equivalents.

What is claimed is:

1. A gas sensor system for monitoring gas concentrations in flue gas generated by a combustor, the gas sensor system comprising:
a gas sensor comprising:
an outer shell disposed in a stream of flue gas in a post-flame zone of the combustor, the outer shall having at least one opening in a fluid communication with the flue gas;
a solid electrolyte cell disposed within the outer shell;
at least one seal cooperating with the electrolyte cell to form a sensing chamber isolated from the flue gas;
a first electrode disposed within the sensing chamber and being isolated from the flue gas so as not to be in a direct fluid contact with the flue gas; and
a second electrode disposed in the outer shell and positioned in close proximity to the at least one opening so as to be in fluid contact with the flue gas, a voltage being generated across the first and second electrodes representing at least two conditions, wherein the first electrode and the second electrode generate a signal comprised of a DC component and a fluctuating AC component, the two conditions comprised of the DC component and a fluctuating AC component; and
the gas sensor system further comprising a processing portion, the processing portion configured to analyze each of the DC component and a fluctuating AC component to determine gas concentrations in the flue gas; and
wherein the first electrode and the second electrode are configured to have different time constants resulting in a measured potential between the first electrode and the second electrode the processing portion configured to analyze the measured potential to represent the fluctuating AC component.

2. The gas sensor system of claim 1, further comprising a reference gas conduit disposed in the sensing chamber and adapted to supply a reference gas to the chamber.

3. The gas sensor system of claim 1, further comprising a conduit disposed within the outer shell and adjacent the electrolyte cell and second electrode, the conduit being in fluid communication with the flue gas.

4. The gas sensor system of claim 3, wherein the conduit delivers a calibration gas in close proximity to the second electrode, the second electrode being effectively calibrated based at least in part on the effect of the calibration gas on the condition sensed by the second electrode.

5. The gas sensor system of claim 4, wherein the calibration gas comprises an essentially fixed concentration of $O_2$.

6. The gas sensor system of claim 3, wherein sample flue gas is extracted from the sensor through the conduit for delivery to a reference gas analyzer.

7. The gas sensor system of claim 1, wherein the solid electrolyte cell is tubular in shape, the sensor comprising two seals disposed substantially at respective ends of the electrolyte cell to cooperate to form the sensing chamber.

8. The gas sensor system of claim 1, further comprising a thermocouple located in close proximity to the electrolyte cell and being adapted to monitor temperature and provide a reference to adjust for varying temperature conditions in the outer shell.

9. The gas sensor system of claim 1, wherein the first electrode is in fluid contact with a reference gas and a voltage signal generated across the first and second electrodes is analyzed to monitor the concentration of gases in the flue gas.

10. The gas sensor system of claim 9, wherein the voltage signal represents the concentration of at least two selected from the group consisting of oxygen, carbon monoxide, and nitric oxide.

11. The gas sensor system of claim 1 further comprising a third electrode disposed within the outer shell and being in fluid communication with the flue gas, the third electrode cooperating with one of the first and second electrodes to sense the concentration of an intended gas in the flue gas, the intended gas being one or a group consisting of oxygen, carbon monoxide, and nitric oxides.

12. The gas sensor system of claim 11, wherein the third electrode is at least in part covered by a filter to react with a second gas in the flue gas to eliminate the effect of the second gas so as to enhance the accuracy of the concentration measured of the intended gas.

13. The gas sensor system of claim 11, wherein the first and second electrodes cooperate to generate a first signal representing the concentration of a first intended gas and the second and third electrodes cooperate to generate a second signal representing the concentration of a second intended gas, the first and second intended gases each being one of a group consisting of oxygen, carbon monoxide, and nitric oxides.

14. The gas sensor system of claim 13, wherein one the first and second signals may be further analyzed to determine the concentration of a third intended gas.

15. The gas sensor system of claim 1, wherein electrical signals representing the gas concentrations respectively sensed by the first and second electrodes are generated, the signals being processed by the system in a time domain to yield combustion parameters, the processing portion calculating the standard deviation of signal fluctuation of the AC component.

16. The gas sensor system of claim 1, wherein the combustor is one of the group consisting of a boiler, a furnace, and a gas turbine.

17. The gas sensor system of claim 1, wherein the combustor includes a burner that generates flue gases, the burner being one selected from the group consisting of a gas-tired burner, a coal-fired burner, an oil-fired burner, and a fossil fuel-fired burner.

18. The gas sensor system of claim 1, wherein the first and second electrodes are made from a material that is porous and catalytic.

19. The gas sensor system of claim 1, wherein the electrolyte cell has one closed end.

20. The gas sensor system of claim 1, wherein the DC component is processed by the processing portion in accordance with the Nernst equation and is used to determine the $O_2$ concentration.

21. The gas sensor system of claim 20, wherein the AC component is processed by the processing portion to determine the concentration of at least one selected from the group consisting of carbon monoxide, nitric oxides and gaseous combustibles.

22. The gas sensor system of claim 1, wherein the DC component is analyzed by the processing portion to determine an $O_2$ concentration in the flue gas.

23. The gas sensor system of claim 22, wherein the fluctuating AC component is analyzed by the processing portion to determine a parameter representing the concentration of combustibles in the flue gas.

24. The gas sensor system of claim 1, wherein the fluctuating AC component is analyzed by the processing portion to determine a concentration in the flue gas of at least one selected from the group consisting of carbon monoxide, and nitric oxides.

25. The gas sensor system of claim 1, wherein a support conduit is disposed in the post flame zone of the combustor and at one end is supported by and affixed to a wall of the combustor, the gas sensor being atone end attached and supported by the support conduit, electrical leads being connected to the first and second electrodes and being disposed in the support conduit at the one end of the support conduit.

26. The gas sensor system of claim 1, wherein the electrolyte cell is comprised of yttria stabilized zirconia.

27. The gas sensor system of claim 1, wherein the electrolyte cell is comprised of zirconia.

28. The gas sensor system of claim 1, wherein the first electrode possesses a first associated time constant and the second electrode possesses a second associated time constant, the first time constant being different than the second time constant; and wherein each of the time constants respectively associated with the first electrode and the second electrode is calculated by the processing portion using a relationship:

$$C_E = C_C + \Delta C_C * (1 - e^{-t/Tc})$$

wherein:
$C_E$=the concentration of oxygen at the electrode,
$C_C$=the concentration of oxygen in the environment,
$\Delta C_C$=the change in concentration of oxygen in the environment,
e=the exponential operator,
t=the time elapsed since the change in oxygen concentration occurred, and
Tc is the time constant specific to the electrode;
wherein each time constant, as calculated by the processing portion, determines how quickly the oxygen concentration level at that electrode changes; and
wherein the processing portion is configured to analyze said relationship.

29. The gas sensor system of claim 1, further comprising a flexible hose connected to the gas sensor, the flexible hose for facilitating the assembly and installation of the gas sensor into said combustor.

30. An emissions monitoring system for monitoring constituent concentration of flue gas components in a combustor, the monitoring system comprising:
a first sampling probe comprising:
an outer shell disposed in a stream of flue gas in a post-flame zone of the combustor, the outer shell having at least one opening for receiving a flue gas;
at least one seal cooperating with the electrolyte cell to form a sensing chamber isolated from the flue gas;
a first electrode disposed within the sensing chamber and being isolated from the flue gas so as not to be in a direct fluid contact with the flue gas;
a second electrode, disposed in the outer shell and positioned in close proximity to the at least one opening so as to be in fluid contact with the flue gas, a voltage being generated across the first and second electrodes representing at least two conditions;
a second sampling probe for monitoring the concentration of a second flue gas component, the second sampling probe comprising:
an outer shell disposed in a stream of flue gas in a post-flame zone of the combustor, the outer shell having at least one opening for receiving a flue gas;
at least one seal cooperating with the electrolyte cell to form a sensing chamber isolated from the flue gas;
a first electrode with an associated time constant disposed within the sensing chamber and being isolated from the flue gas so as not to be in a direct fluid contact with the flue gas;
a second electrode with an associated time constant that is different from the time constant associated with the first electrode, disposed in the outer shell and positioned in close proximity to the at least one opening so as to be in fluid contact with the flue gas, a voltage being generated across the first and second electrodes representing at least two conditions; and at least one analyzer having inputs for monitoring the receiving the voltages generated by the first anti second sampling probes and having a processor for analyzing the voltage data to determine the concentrations of the first and second flue gas components, the voltage data includes a DC component and a fluctuating AC component, the analyzer analyzing each of the DC component and a fluctuating AC component to determine the constituent concentration of flue gas components; and wherein the first electrode and the second electrode are configured to have different time constants resulting in a measured potential between the first electrode and the second electrode, the analyzer configured to analyze the measured potential to represent the fluctuating AC component.

31. The monitoring system of claim 30, wherein the first electrode, of the first sampling probe, possesses a first associated time constant and the second electrode, of the first sampling probe, possesses a second associated time constant, the first time constant being different than the second time constant; and wherein each of the time constants respectively associated with the first electrode and second electrode is calculated by the analyzer using a relationship:

$$C_E = C_C + \Delta C_C * (1 - e^{-1/Tc})$$

wherein:

$C_E$ = the concentration of oxygen at the electrode, $C_C$ = the concentration of oxygen in the environment, $\Delta C_C$ = the change in concentration of oxygen in the environment, e = the exponential operator, t = the time elapsed since the change in oxygen concentration occurred, and Tc is the time constant specific to the electrode;

wherein each time constant, as calculated by the analyzer, determines how quickly the oxygen concentration level at that electrode changes; and wherein the analyzer is configured to analyze said relationship.

32. The monitoring system of claim 30, further comprising a flexible hose connected to at least one of the first sampling probe and the second sampling probe, the flexible hose for facilitating the assembly and installation of at least one of the first sampling probe and the second sampling probe into said combustor.

33. The monitoring system of claim 30, wherein the analyzer:

analyzing the DC component to determine an $O_2$ concentration in the flue gas; and analyzing the fluctuating AC component to determine a parameter representing the concentration of combustibles in the flue gas.

* * * * *